(12) United States Patent
Larsen et al.

(10) Patent No.: US 11,547,433 B2
(45) Date of Patent: Jan. 10, 2023

(54) DEVICES FOR MANIPULATING TISSUE AND RELATED METHODS

(71) Applicant: Boston Scientific Scimed, Inc., Maple Grove, MN (US)

(72) Inventors: Steven Larsen, Lino Lakes, MN (US); Brian Hanson, Shoreview, MN (US); Elias Khoury, Maple Grove, MN (US); Ismail Guler, Maple Grove, MN (US); Paul Smith, Smithfield, RI (US); Daniel Vancamp, Elk River, MN (US); Wade Strelow, Maple Grove, MN (US); Kevin McElwee, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 480 days.

(21) Appl. No.: 16/722,525

(22) Filed: Dec. 20, 2019

(65) Prior Publication Data

US 2020/0121350 A1    Apr. 23, 2020

Related U.S. Application Data

(63) Continuation of application No. 15/216,162, filed on Jul. 21, 2016, now Pat. No. 10,548,625.
(Continued)

(51) Int. Cl.
| A61B 17/3205 | (2006.01) |
| A61B 17/221 | (2006.01) |
| A61B 90/00 | (2016.01) |

(52) U.S. Cl.
CPC ...... *A61B 17/32056* (2013.01); *A61B 17/221* (2013.01); *A61B 2017/2212* (2013.01); *A61B 2090/08021* (2016.02)

(58) Field of Classification Search
CPC ... A61B 17/221; A61B 17/28; A61B 17/2804; A61B 17/282; A61B 17/32056;
(Continued)

(56) References Cited

U.S. PATENT DOCUMENTS

| 2,054,149 A | 9/1936 | Wappler |
| 5,207,686 A | 5/1993 | Dolgin |

(Continued)

FOREIGN PATENT DOCUMENTS

DE    10117836 C1    7/2002

OTHER PUBLICATIONS

International Search Report and Written Opinion issued in PCT International Application No. PCT/US2016/043453, dated Oct. 4, 2016, 13 pages.

*Primary Examiner* — Sarah W Aleman
(74) *Attorney, Agent, or Firm* — Bookoff McAndrews, PLLC

(57) ABSTRACT

A medical device may include an insertion device having a proximal end, a distal end, and a lumen extending therethrough. The medical device may further include a snare device configured to transition between a contracted state within the lumen of the insertion device, and an expanded state extending distally of the insertion device. The snare device may include a loop including a pair of legs and a distal tip. The distal tip may include a plurality of stabilizers between the pair of legs.

17 Claims, 7 Drawing Sheets

Related U.S. Application Data

(60) Provisional application No. 62/196,524, filed on Jul. 24, 2015.

(58) Field of Classification Search
CPC ..... A61B 2017/2212; A61B 2017/2945; A61F 2/01; A61F 2/00063
See application file for complete search history.

(56) References Cited

U.S. PATENT DOCUMENTS

| | | | |
|---|---|---|---|
| 6,152,922 A | 11/2000 | Ouchi | |
| 7,491,211 B2 | 2/2009 | Ziegler | |
| 8,206,401 B2 * | 6/2012 | Nakao | A61B 17/32056 606/127 |
| 8,974,470 B2 * | 3/2015 | Lampropoulos | A61B 17/221 606/113 |
| 9,498,238 B2 * | 11/2016 | Smith | A61B 18/14 |
| 9,770,252 B2 * | 9/2017 | Smith | A61B 17/32056 |
| 2003/0018355 A1 | 1/2003 | Goto et al. | |
| 2005/0227529 A1 | 10/2005 | Mrakovich et al. | |
| 2005/0261706 A1 | 11/2005 | Cheng et al. | |
| 2005/0267492 A1 | 12/2005 | Poncet et al. | |
| 2006/0058813 A1 | 3/2006 | Teague et al. | |
| 2007/0016224 A1 | 1/2007 | Nakao | |
| 2008/0249553 A1 | 10/2008 | Gruber et al. | |
| 2012/0172662 A1 | 7/2012 | Kappel et al. | |
| 2012/0172864 A1 | 7/2012 | Farin et al. | |
| 2012/0283723 A1 * | 11/2012 | Jenkins | A61B 18/14 606/41 |
| 2013/0103041 A1 * | 4/2013 | Regadas | A61B 17/32056 606/113 |
| 2014/0188156 A1 | 7/2014 | Tekulve et al. | |
| 2015/0100062 A1 | 4/2015 | Smith et al. | |
| 2015/0105789 A1 | 4/2015 | Raybin et al. | |
| 2015/0157345 A1 * | 6/2015 | Haack | A61B 17/32056 606/113 |

* cited by examiner

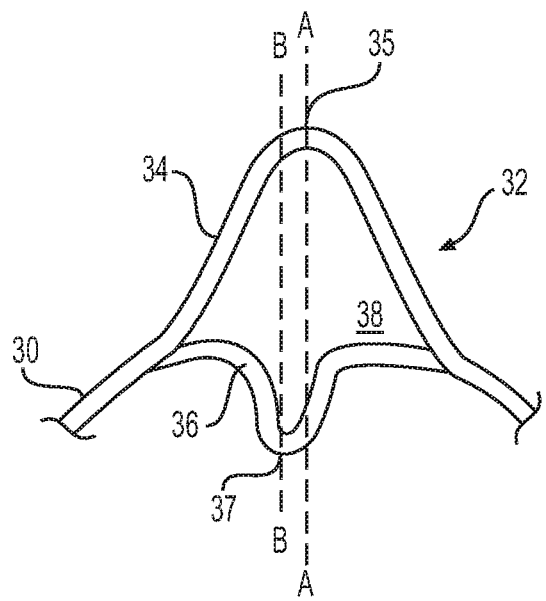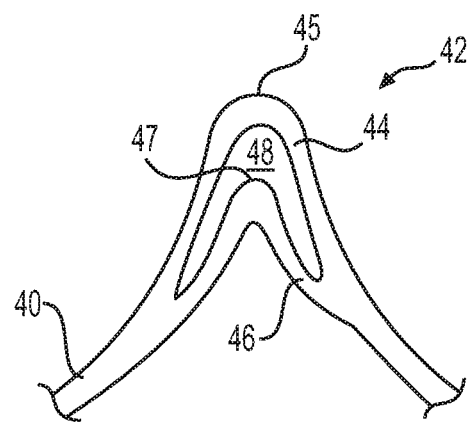
FIG. 2  FIG. 3
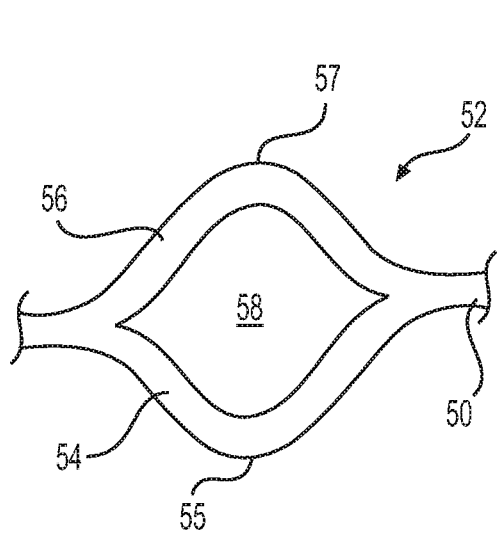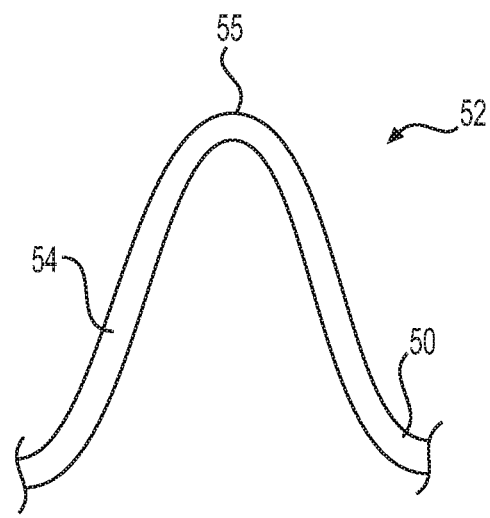
FIG. 4A  FIG. 4B

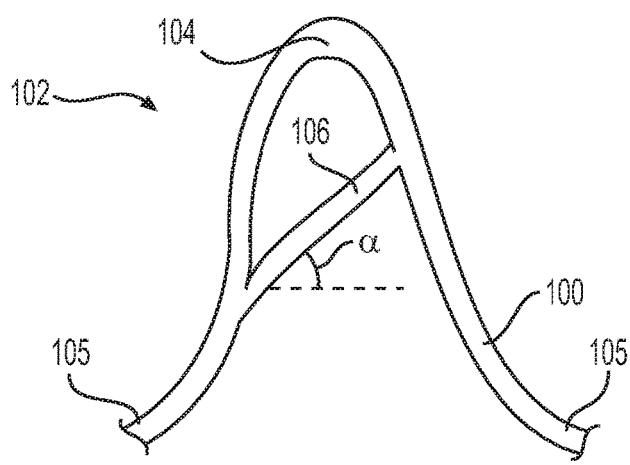 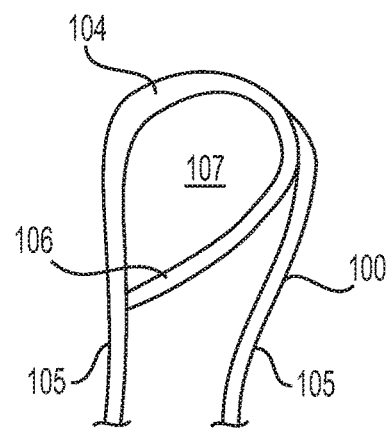
*FIG. 9A*  *FIG. 9B*
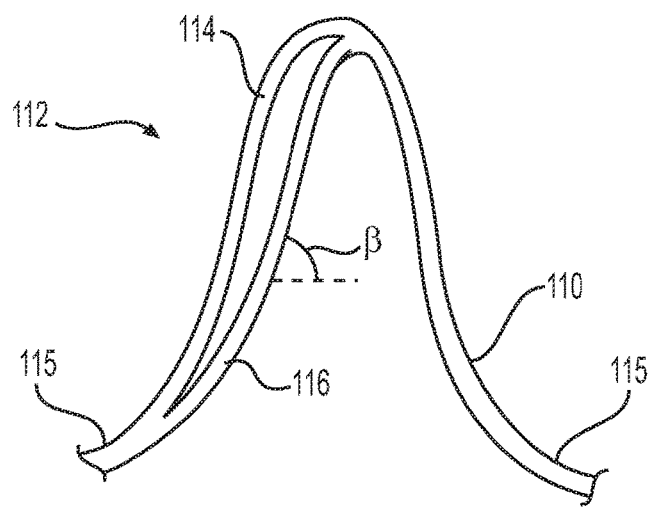 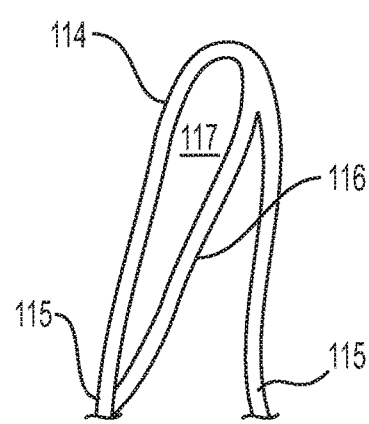
*FIG. 10A*  *FIG. 10B*
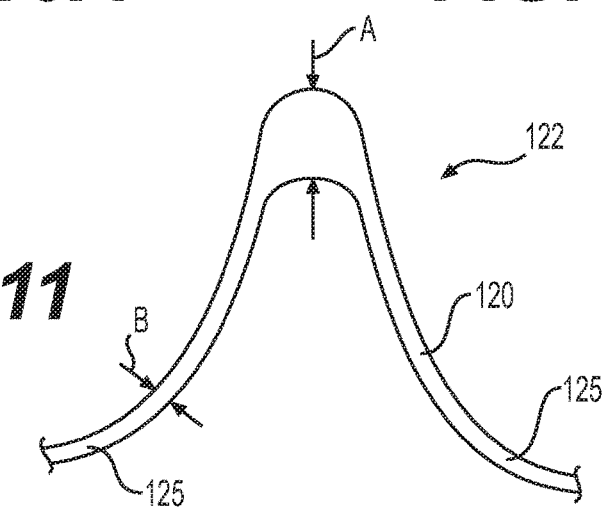
*FIG. 11*

DEVICES FOR MANIPULATING TISSUE AND RELATED METHODS

CROSS-REFERENCE TO RELATED APPLICATIONS

This application is a continuation of U.S. application Ser. No. 15/216,162, filed on Jul. 21, 2016, which claims the benefits of priority from U.S. Provisional Application No. 62/196,524, filed on Jul. 24, 2015, the entireties of which are incorporated herein by reference.

TECHNICAL FIELD

Aspects of the present disclosure generally relate to medical devices and procedures. In particular, aspects of the present disclosure relate to medical devices for, for example, manipulating, resecting, grasping, and/or collecting tissue, such as, for example, snare devices.

BACKGROUND

Medical devices, such as endoscopes or other suitable introduction devices, are employed for a variety of diagnostic and surgical procedures, such as endoscopy, laparoscopy, arthroscopy, gynoscopy, thoracoscopy, and cystoscopy, etc. Many of these procedures are carried out for purposes of tissue resection, which generally includes removal of tissue of an organ or a gland to treat tumors, infestations, and the like. In particular, such procedures may be carried out by inserting an insertion device into a patient's body through a surgical incision, or via a natural anatomical orifice (e.g., mouth, vagina, or rectum), and performing the procedure or operation.

Snare devices, in particular, have been used in many medical procedures, including Endoscopic Mucosal Resection (EMR) and Endoscopic Sub-mucosal Resection (ESR), polypectomy, mucosectomy, etc., for resecting tissue from a target site. A snare device generally includes a snare loop formed by snare wire(s), which engages the tissue intended to be resected. The snare loop may include teeth or similar structures configured to cut and or grasp tissue. The snare loop is controlled and operated at a proximal end of the device through a suitable actuating mechanism. However, in many conventional snare devices and snares with thin atraumatic tips, the snare loop may have a tendency to twist about itself (for example, about a longitudinal axis of the device), away from a plane of a layer of tissue, which may reduce the snare's ability to ensnare the desired tissue.

SUMMARY

Examples of the present disclosure relate to, among other things, medical devices such as snares, and related methods of use thereof. Each of the examples disclosed herein may include one or more of the features described in connection with any of the other disclosed examples.

In one example, a medical device may include an insertion device having a proximal end, a distal end, and a lumen extending therethrough. The medical device may further include a snare device configured to transition between a contracted state within the lumen of the insertion device, and an expanded state extending distally of the insertion device. The snare device may include a loop including a pair of legs and a distal tip. The distal tip may include a plurality of stabilizers between the pair of legs.

The medical device may further include one or more of the following features. The plurality of stabilizers may include a first stabilizer defining a first peak and a second stabilizer defining a second peak. The first peak may be a distal-most point of the first stabilizer and the second peak may be a proximal-most point of the second stabilizer. The first peak may be a distal-most point of the first stabilizer and the second peak may be a distal-most point of the second stabilizer. A distance of the first peak from a central longitudinal axis of the snare device may be different than a distance of the second peak from the central longitudinal axis of the snare device. The first peak may be on a first side of a plane of the loop and the second peak may be on a second side of the plane of the loop. At least one of the first stabilizer and the second stabilizer may be asymmetric relative to a central longitudinal axis of the snare device. The second stabilizer may have a cross-sectional dimension larger than a cross-sectional dimension of the first stabilizer. The cross-sectional dimension may be a thickness. The first stabilizer may include a first shape, and the second stabilizer may include a second shape. The first shape may be different than the second shape. Alternatively, the first shape may be the same as the second shape. When the snare device is in the expanded state, a central portion of the second stabilizer may extend at angle of greater than 60° with respect to an axis perpendicular to a longitudinal axis of the snare device. The first stabilizer may be contiguous with the pair of legs and the second stabilizer may be a discrete strut affixed to the pair of legs. The first stabilizer and the second stabilizer may each be contiguous with the pair of legs. Further, the loop may be formed of a heat set monofilament or multifilament wire.

In another example, a medical device may include an insertion device having a proximal end, a distal end, and a lumen extending therethrough. The medical device may further include a snare device configured to transition between a contracted state within the lumen of the insertion device, and an expanded state extending distally of the insertion device. The snare device may include a loop having a pair of legs and a distal tip. Further, the medical device may include a securement member disposed about the tip and configured to receive the loop therethrough.

The medical device may further include one or more of the following features. The securement member may define a pair of channels, each channel of the pair of channels may be configured to receive a portion of the loop therethrough. Additionally, each channel may be sized so as to limit translation of the portions of loop disposed within the channels towards one another and rotational movement of the portions of loop disposed within the channels about one another. The securement member may include a clam shell construction.

In another example, a medical device may include an insertion device having a proximal end, a distal end, and a lumen extending therethrough. The medical device may further include a snare device configured to transition between a contracted state within the lumen of the insertion device, and an expanded state extending distally of the insertion device. The snare device may include a wire overlapped upon itself so as to form a first loop and a second distal loop including a distal tip. The medical device may further include a securement mechanism for securing the overlapped portions of the wire together.

The medical device may further include one or more of the following features. The wire may include a varied cross-section along its length, wherein a first portion of the wire includes a rectangular cross-section, a second portion of the wire includes a circular cross-section, a third portion of the wire includes a wedge-shaped opening, and a fourth portion of the wire includes an edge angled relative to a plane perpendicular to the plane of the first loop. Additionally or alternatively, the edge may be sharp.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIG. 2 depicts a side view of an exemplary atraumatic tip of a snare device according to a further example.

FIG. 3 depicts a side view of an exemplary atraumatic tip of a snare device according to another example.

FIGS. 4A and 4B depict exemplary top and side views, respectively, of an exemplary atraumatic tip of a snare device according to a still further example.

FIG. 9A depicts a side view of an exemplary atraumatic tip of a snare device according to yet another example, in an extended state.

FIG. 9B depicts a side view of the exemplary atraumatic tip of FIG. 9A, in a retracted and/or compressed state.

FIG. 10A depicts a side view of an exemplary atraumatic tip of a snare device according to a still further example, in an extended state.

FIG. 10B depicts a side view of the exemplary atraumatic tip of FIG. 10A, in a retracted and/or compressed state.

FIG. 11 depicts a side view of an exemplary atraumatic tip of a snare device according to a further example.

DETAILED DESCRIPTION

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body or closer to a medical professional using the medical device. In contrast, "distal" refers to a position relatively further away from the medical professional using the medical device, or closer to the interior of the body.

Figure 1A:
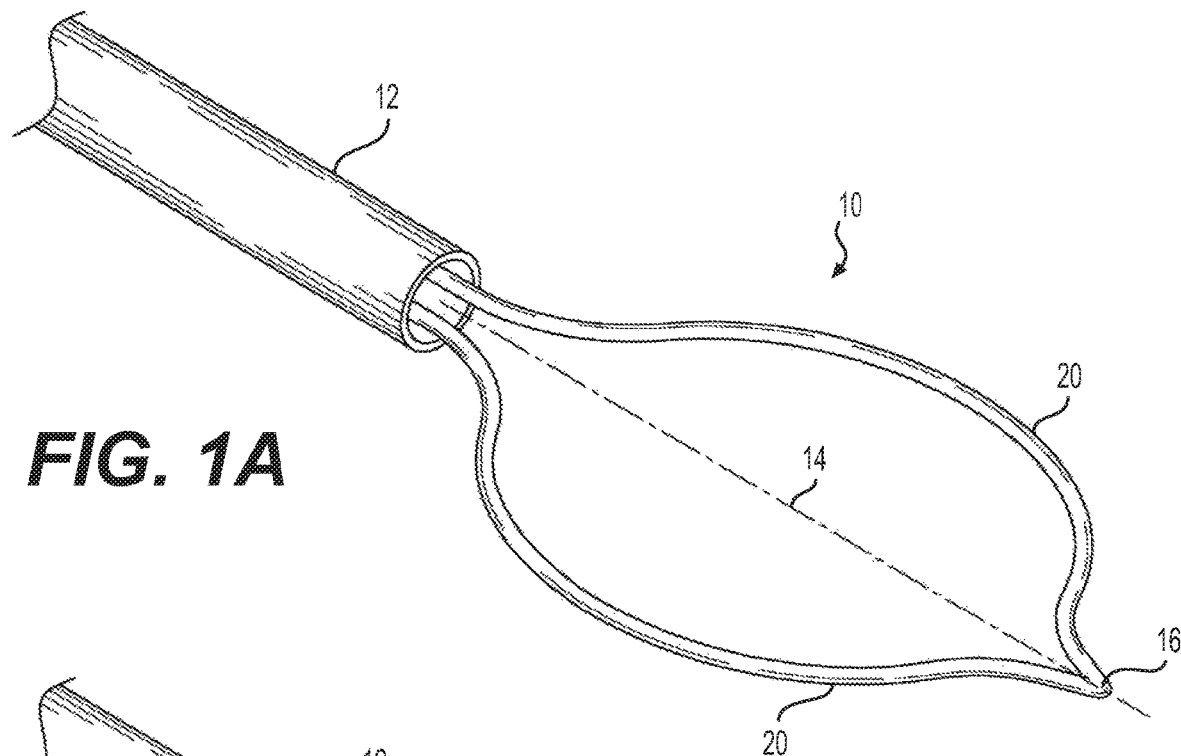
FIG. 1A depicts an exemplary snare device in an extended and expanded state.

The present disclosure is drawn to medical devices such as snare devices, and related methods of use thereof. FIG. 1A depicts a snare device 10. Snare device 10 may be delivered to a target tissue via an insertion device 12. Insertion device 12 may include any device configured to deliver medical instruments, such as snare device 10, into a subject's body. Insertion device 12 may be inserted into a variety of body openings, lumens, and/or cavities. For example, insertion device 12 may be inserted into any portion of a urinary tract, such as a ureter, a gastrointestinal lumen, such as an esophagus or colon, a vascular lumen, and/or an airway. According to aspects of the present disclosure, insertion device 12 may be a ureteroscope, an endoscope, a hysteroscope, a uteroscope, a bronchoscope, a cystoscope, and similar devices. Alternatively, insertion device 12 may be a catheter or other sheath. Insertion device 12 may be single-use and disposable, or multiple-use and non-disposable. Insertion device 12 may have a circular cross-sectional shape defining an inner lumen, but other suitable cross-sectional shapes such as elliptical, oval, polygonal, or irregular may also be employed.

Once positioned within the subject's body, a medical professional may move snare device 10 between an extended state (FIG. 1A) and a retracted state (not shown). In the extended state, snare device 10 may extend distally out of the distal end of insertion device 12, and snare device 10 may be caused to expand to surround or otherwise engage, grasp, and/or collect tissue. In moving from the extended state to the retracted state, snare device 10 may be drawn into the distal end of insertion device 12, and snare device 10 may be caused to contract to resect tissue.

For example, snare device 10 may be a single, continuous monofilament or multifilament piece of material, such as a wire, including legs 20 formed in a loop. The snare loop may further include teeth or the like (not shown) configured for cutting and/or grasping tissue therewith. Legs 20 may extend proximally to a proximal portion (not shown) of medical device 10 where legs 20 may be associated with any appropriate user interface such as, for example, a handle (not shown). Alternatively, legs 20 may terminate proximally of a handle. As such, a proximal end of legs 20 may be coupled to an actuating member (not shown) via a securement device such as, for example, a hypotube or crimp (not shown). The handle may be configured to remain outside of the patient's body during a procedure and may allow a user to control snare device 10, for example, by applying an axially directed pushing or pulling force on one or both of the legs 20, to extend legs 20 out of the distal end of insertion device 12 or retract legs 20 into the distal end of insertion device 12, respectively.

Figure 1B:
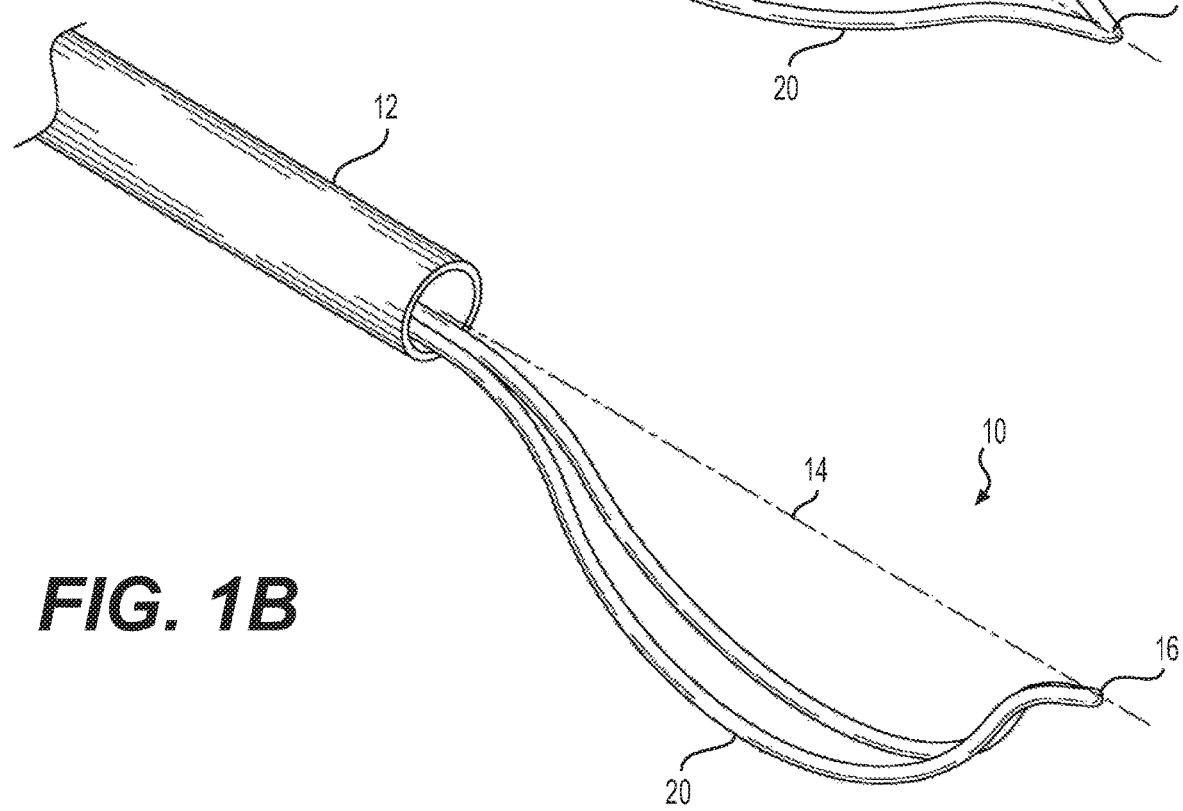
FIG. 1B depicts the exemplary snare device of FIG. 1A in an extended and folded state.

Snare device 10 may be formed of any appropriate material, such as, for example, Nitinol. Snare device 10 may be heat set into an arcuate, circular, or otherwise curved shape as shown in FIG. 1A, and may include an atraumatic tip 16. However, such a heat set construction may result in instability as there is more than one position or configuration of snare device 10. For example, as shown in FIG. 1B, as snare device 10 impacts tissue to be resected, grasped, and/or collected, or as snare device 10 is drawn proximally towards insertion device 12, snare device 10 may twist, fold, and/or rotate about longitudinal axis 14 onto itself, similar to the construction shown in FIG. 1B. That is, upon impact with tissue and/or while being drawn into insertion device 12, the increased stress and/or strain imparted to snare device 10 may cause instability or torsion in snare device 10. This torsional instability in the snare device 10 may cause snare device 10 to flip into an unwanted configuration as shown in FIG. 1B.

FIGS. 2 and 3 depict side-views of exemplary constructions of the distal end of a snare device having an atraumatic tip with one or more added stabilizers. The examples of FIGS. 2 and 3 may include one or more features described above in connection with FIGS. 1A and 1B. Additionally or alternatively, as shown in FIG. 2, an exemplary snare device 30 may include an atraumatic tip 32 having a first stabilizer 34 defining a first peak 35 and a second stabilizer 36 defining a second peak 37. As shown in FIG. 2, first peak 35 defines a distal-most point of first stabilizer 34 while second peak 37 defines a proximal-most point of second stabilizer 36. That is, second stabilizer 36 may extend proximally toward a proximal end of snare device 30 along a common plane as legs 20 of snare device 30 while first stabilizer 34 extends in a distal direction. Additionally, first stabilizer 34 and second stabilizer 36 collectively define a space 38 therebetween. Second stabilizer 36 may span a width of atraumatic tip 32 and have a generally U-shaped, V-shaped, or sinusoidally-shaped construction.

Further, as shown in FIG. 3, an exemplary snare device 40 may include an atraumatic tip 42 having a first stabilizer 44 defining a first peak 45 and a second stabilizer 46 defining a second peak 47. As shown in FIG. 3, first peak 45 defines a distal-most point of first stabilizer 44 while second peak 47 defines a distal-most point of second stabilizer 46. That is, each of first stabilizer 44 and second stabilizer 46 may extend in a distal direction along a common plane as legs 20 of snare device 40. Additionally, first stabilizer 44 and second stabilizer 46 collectively define a space 48 therebetween. Second stabilizer 46 may span a width of atraumatic tip 42 and may generally have an inverted U-shape, an inverted V-shape, or sinusoidally-shaped construction.

As shown in FIG. 2, for example, one or both of stabilizers 34 and 36 may be a separate member fixed to snare device 30. For example, second stabilizer 36 may be a separate and distinct element affixed to snare device 30 via soldering, welding, adhesives, and/or any other appropriate method. First stabilizer 34, may be contiguous with snare device 30. That is, as shown in FIG. 2, first stabilizer 34 may be monolithically formed of a common wire or member as legs 20 of snare device 30. Alternatively, as shown in FIG. 3, both of first stabilizer 44 and second stabilizer 46 may be contiguous with legs 20 of snare device 40. Such a construction may be produced via laser cutting a metal frame, for example.

Second stabilizers 36, 46 may facilitate increased stability in snare devices 30, 40 by preventing snare devices 30, 40 from bending and/or deflecting away from a plane of a layer of tissue, which may reduce the snare's ability to ensnare the desired tissue during resecting, grasping, and/or collecting tissue via snare devices 30, 40. For example, inclusion of a second stabilizer 36, 46, spanning the width of atraumatic tip 32, 42, may act to urge an associated snare device 30, 40 towards an open loop configuration. That is, second stabilizers 36 and 46 may resist forces (e.g., torsional forces) imparted to snare devices 30, 40, respectively, during use, that would otherwise urge snare devices 30 and 40 to twist, fold, and/or rotate about an associated longitudinal axis of snare device 30 and 40, onto itself, similar to the construction shown in FIG. 1B. For example, the inclusion of second stabilizer 36, 46, axially spaced (e.g., by space 38, 48) along a longitudinal axis from first stabilizer 34, 44, respectively, enables an increasingly consistent distribution of forces during use of snare devices 30, and 40.

Additionally, as shown in FIG. 2, for example, each of peaks 35 and 37 may be offset from one another. That is, a central longitudinal axis A-A through peak 35 extending parallel to the central longitudinal axis of snare device 30 may be offset or parallel with a central longitudinal axis B-B through peak 37 extending parallel to the central longitudinal axis of snare device 30. That is, peaks 35 and 37 may be spaced from one another along a plane extending transverse to a longitudinal axis of snare device 30. Such an offset arrangement of peaks 35 and 37 may inhibit twisting, folding, and/or rotation about the longitudinal axis of snare device 30. While not shown, the peaks 45 and 47 of snare device 40 may optionally be offset from one another.

Further, one or more of first stabilizers 34, 44, and second stabilizers 36, 46 may be enlarged with respect to a remainder of snare device 30, 40, respectively. That is, for example, one or both of first stabilizer 34 and second stabilizer 36 of snare device 30 may have a cross-sectional dimension (e.g., thickness, diameter) larger (not shown) than another portion of snare device 30. For example, as shown in FIG. 11, one or more portions of snare device 30, 40 may have an enlarged dimension, as will be described in further detail below. In such a manner, snare device 30, 40 may be further prevented from twisting, folding, and/or rotating about the longitudinal axis of snare device 30, 40. Additionally, although not shown, additional stabilizers may be included without departing from the scope of this disclosure. For example, snare devices 30, 40 may have between 2 and 4 stabilizers. Alternatively, a greater number of stabilizers may be used.

FIGS. 4A and 4B depict top and side-views, respectively, of an exemplary construction of the distal end of a snare device having an atraumatic tip with multiple stabilizers. The example of FIGS. 4A and 4B may include one or more features described above in connection with FIGS. 1A and 1B. Additionally or alternatively, as shown in FIG. 4A, an exemplary snare device 50 may include an atraumatic tip 52 having a first stabilizer 54 defining a first peak 55 and a second stabilizer 56 defining a second peak 57. As shown in FIG. 4A, first stabilizer 54 extends in a first direction out of the plane defined by legs 20 of snare device 50 and second stabilizer 56 extends in an opposite direction of first stabilizer 54. That is, second stabilizer 56 may extend in a second direction, opposite the first direction, out of the plane defined by legs 20 of snare device 50. Accordingly, first stabilizer 54 and second stabilizer 56 may define an opening 58 therebetween. Peaks 55, 57 may each be positioned at a distal-most end of snare device 50. Each of stabilizers 54 and 56, may converge toward the plane of legs 20 of snare device 50 when transitioning from an expanded state to a contracted state such that opening 58 closes upon contraction into an insertion device 12. Each of stabilizers 54 and 56, as shown in FIG. 4A, may be contiguous with legs 20 of snare device 50. That is, first stabilizer 54 and second stabilizer 56 may be may be monolithically formed of a common wire or member as legs 20 of snare device 50 (e.g., via laser cutting or similar methods). Alternatively, one or both of stabilizers 54, 56 may be a separate and distinct member fixed to snare device 50, for example, via soldering, welding, adhesives, and/or any other appropriate method.

Stabilizers 54, 56 may facilitate increased stability in snare device 50 by preventing snare device 50 from bending and/or deflecting away from a plane of a layer of tissue, which may reduce the snare's ability to ensnare the desired tissue during resecting, grasping, and/or collecting tissue via snare device 50. That is, first stabilizer 54 and second stabilizer 56 may resist forces (including torsional forces) imparted to snare device 50 during use that would otherwise urge snare device 50 to twist, fold, and/or rotate about a longitudinal axis of snare device 50, onto itself, similar to the construction shown in FIG. 1B. For example, the inclusion of multiple stabilizers 54 and 56, axially spaced along a plane transverse to a longitudinal axis of snare device 50, enables an increasingly consistent distribution of forces during use of snare device 50.

Additionally, each of peaks 55 and 57 may be offset from one another, similar to peaks 35 and 37 of FIG. 2 being offset on axes A-A and B-B. Such an offset arrangement of peaks 55 and 57 may inhibit twisting, folding, and/or rotation about the longitudinal axis of snare device 50. Additionally or alternatively, peaks 55 and 57 may also be offset from one another such that one of peaks 55 and 57 extends further distally than the other of peaks 55 and 57, similar to the example shown in FIG. 3. Further, one or both of first stabilizer 54 and second stabilizer 56 may be enlarged with respect to a remainder of snare device 50. That is, for example, one or both of first stabilizer 54 and second stabilizer 56 of snare device 50 may have a cross-sectional dimension (e.g., thickness, diameter) larger (not shown) than another portion of snare device 50. In such a manner, snare device 50 may be further prevented from twisting, folding, and/or rotating about the longitudinal axis of snare device 50. Additionally, although not shown, it is noted that additional stabilizers may be included without departing from the scope of this disclosure. For example, snare device 50 may have between 2 and 4 stabilizers. Alternatively, a greater number of stabilizers may be used.

Figure 5:
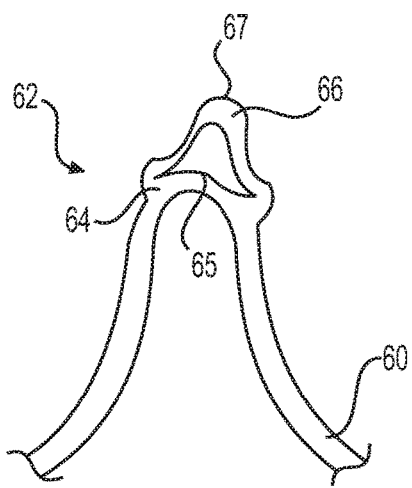
FIGS. 5-8 each depicts a side view of an exemplary atraumatic tip of a snare device according to additional examples.

FIGS. 5-8 depict side-views of exemplary constructions of the distal end of a snare device having an atraumatic tip with one or more additional stabilizers. The examples of FIGS. 5-8 may include one or more features described above in connection with FIGS. 1A and 1B. Additionally or alternatively, as shown in FIG. 5, an exemplary snare device 60 may include an atraumatic tip 62 having a first stabilizer 64 defining a first peak 65 and a second stabilizer 66 defining a second peak 67. As shown in FIG. 5, first stabilizer 64 and second stabilizer 66 may extend in a distal direction along a common plane as legs 20 of snare device 60. Second stabilizer 66 may extend distally of first stabilizer 64. Further, second stabilizer 66 may be irregularly shaped. That is, second stabilizer 66 may include any non-uniform, free form, and/or asymmetric shape different than first stabilizer 64. Further, it is noted that the diameter of the monofilament or multifilament wire of legs 20 of snare device 60 may be varied. That is, a width of the diameter of the wire of snare device 60 at or adjacent second peak 67, and/or at or adjacent one or more connection points between first stabilizer 64 and second stabilizer 66, may be enlarged relative to the remainder of the wire of snare device 60. For example, the enlarged portions may be in the form of bulged portions of the wire of snare device 60. It is also contemplated that enlarged portions may be formed at similar locations on snare devices 30 and/or 40.

Figure 6:
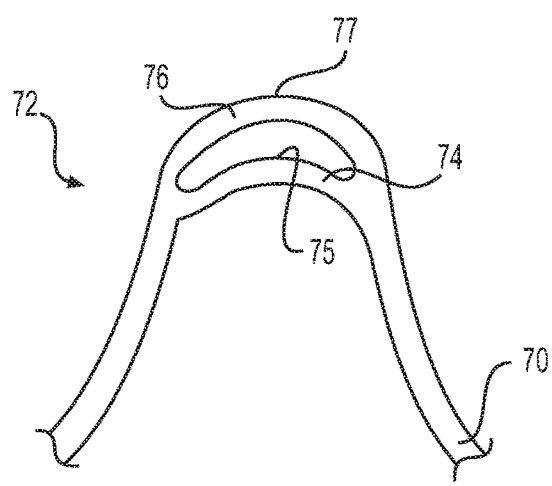

Further, as shown in FIG. 6, an exemplary snare device 70 may include an atraumatic tip 72 having a first stabilizer 74 defining a first peak 75 and a second stabilizer 76 defining a second peak 77. As shown in FIG. 6, first stabilizer 74 and second stabilizer 76 may extend in a distal direction along a common plane as legs 20 of snare device 70. Second stabilizer 76 may extend distally of first stabilizer 74. Further, second stabilizer 76 may be similarly shaped as first stabilizer 74. That is, first and second stabilizers 74 and 76 may include a common shape and/or dimension.

Figure 7:
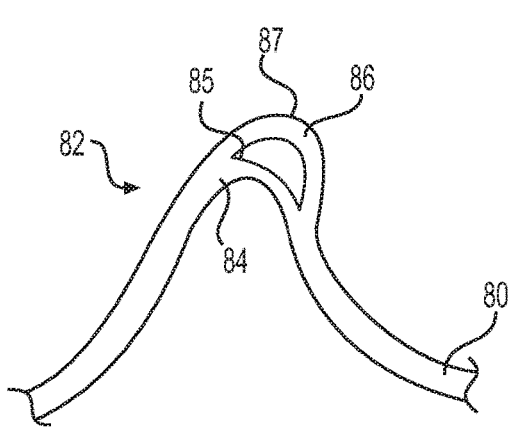

Additionally, as shown in FIG. 7, an exemplary snare device 80 may include an atraumatic tip 82 having a first stabilizer 84 defining a first peak 85 and a second stabilizer 86 defining a second peak 87. As shown in FIG. 7, first stabilizer 84 and second stabilizer 86 may extend in a distal direction along a common plane as legs 20 of snare device 80. Second stabilizer 86 may extend asymmetrically relative to first stabilizer 84. That is, second stabilizer 86 may extend in a direction offset from a central longitudinal axis of snare device 80. Additionally, as shown in FIG. 7, one or more of first peak 85 and second peak 87 may be offset from a central longitudinal axis of snare device 80.

Figure 8:
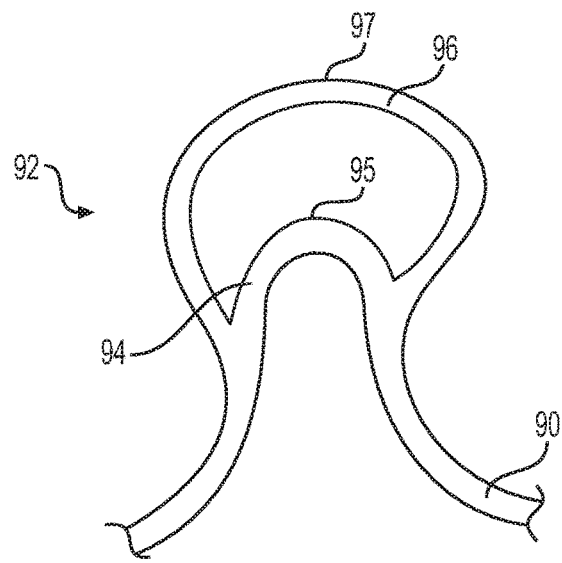

Further, as shown in FIG. 8, an exemplary snare device 90 may include an atraumatic tip having a first stabilizer 94 defining a first peak 95 and a second stabilizer 96 defining a second peak 97. As shown in FIG. 8, first and second stabilizers 94 and 96 extend in a distal direction along a common plane as legs 20 of snare device 90. Second stabilizer 96 may extend distally of first stabilizer 94 and may be enlarged so as to balloon, swell, protrude or otherwise bulge outwardly. It is contemplated that the wire forming snare device 70, 80, and/or 90 may have a constant thickness.

Multiple stabilizers 64, 66, 74, 76, 84, 86, 94, and 96 may facilitate increased stability in snare devices 60, 70, 80, and 90, respectively, by preventing snare devices 60, 70, 80, and 90 from bending and/or deflecting away from a plane of a layer of tissue, which may reduce the snare's ability to ensnare the desired tissue during resecting, grasping, and/or collecting tissue via snare devices 60, 70, 80, and 90. That is, stabilizers 64, 66, 74, 76, 84, 86, 94, and 96 may resist forces (including torsional forces) imparted to snare devices 60, 70, 80, and 90 during use that would otherwise urge snare devices 60, 70, 80, and 90 to twist, fold, and/or rotate about an associated longitudinal axis of snare device 60, 70, 80, and 90, onto itself, for example, as shown in FIG. 1B.

In some arrangements, for example, stabilizers 64, 66, 74, 76, 84, 86, 94, and 96, may be axially spaced from one another along a longitudinal axis of snare device 60, 70, 80, and 90, respectively. Such a spacing may enable an increasingly consistent distribution of forces during use of snare devices 60, 70, 80, and 90. Additionally, as shown in FIGS. 5 and 7, for example, peaks 67, 87 may be offset from peaks 65, 85. That is, a central longitudinal axis through peak 67, 87 extending parallel to the central longitudinal axis of snare device 60, 80, respectively, may be offset with a central longitudinal axis through peak 65, 85 extending parallel to the central longitudinal axis of snare device 60, 80, respectively, similar to the configuration shown in FIG. 2. Such an offset arrangement of peaks may inhibit twisting, folding, and/or rotation about the longitudinal axis of snare device 60, 80. While not shown, the peaks 75 and 77 of snare device 70 may optionally be offset from one another, while peaks 95 and 97 of snare device 90 may be optionally offset from one another.

Further, one or more of stabilizers 64, 66, 74, 76, 84, 86, 94, and 96, may be enlarged (e.g., may have a larger cross-sectional dimension) with respect to a remainder of snare device 60, 70, 80, and 90, respectively. In such a manner, snare devices 60, 70, 80, and 90 may be further prevented from twisting, folding, and/or rotating about a respective longitudinal axis of snare device 60, 70, 80, and 90. Additionally, although not shown, that additional stabilizers may be included without departing from the scope of this disclosure. For example, snare devices 60, 70, 80, and 90 may have between 2 and 4 stabilizers. Alternatively, a greater number of stabilizers may be used.

FIGS. 9A, 9B, 10A, and 10B depict side-views of exemplary constructions of the distal end of a snare device having an atraumatic tip with one or more additional stabilizers. The exemplary constructions of FIGS. 9A, 9B, 10A, and 10B may facilitate improved packing or retraction of snare devices within an insertion device. For example, as shown in FIG. 9A, an exemplary snare device 100 may include an atraumatic tip 102 having a first stabilizer 104 and a second stabilizer 106. As shown in FIG. 9A, first and second stabilizers 104 and 106 may extend along a common plane with legs 105 of snare device 100. Second stabilizer 106 may extend at an angle between legs 105 of snare device 100. For example, as shown in FIG. 9A, second stabilizer 106 may extend at an angle $\alpha$ with respect to an axis perpendicular to a longitudinal axis of snare device 100. Angle $\alpha$ may be between, for example, 0° and 60°. For example, angle $\alpha$ may be about 45°. As used herein, the terms "about," "substantially," and "approximately," may indicate a range of values within +/−5% of a stated value. As shown in FIG. 9B, upon retraction into or packing within an insertion device, such as, for example, insertion device 12, snare device 100 may compress. However, due to the angle $\alpha$ of second stabilizer 106, a relatively large gap 107 may remain between second stabilizer 106 and first stabilizer 104 of snare device 100.

Alternatively, as shown in FIG. 10A, an exemplary snare device 110 may include an atraumatic tip 112 having a first stabilizer 114 and a second stabilizer 116. As shown in FIG. 10A, first and second stabilizers 114 and 116 may extend along a common plane with legs 115 of snare device 110. Second stabilizer 116 may extend at angle between legs 115 of snare device 110. For example, as shown in FIG. 10A, second stabilizer 116 may extend at an angle $\beta$ with respect to an axis perpendicular to a longitudinal axis of snare device 110. Angle $\beta$ may between, for example, 45° and 180°. For example, angle $\beta$ may be about 75°. As shown in FIG. 10B, upon retraction into or packing within an insertion device, such as, for example, insertion device 12, medical device 110 may compress. However, due to the larger angle $\beta$ of second stabilizer 116 (relative to the smaller angle $\alpha$ in FIG. 9A), a gap 117 may remain between second stabilizer 116 and first stabilizer 114 of snare device 110. As shown, gap 117 may be relatively more narrow than gap 107. That is, the angles $\alpha$ and $\beta$ may be selected to provide varied snare device 100, 110 profiles enabling a relatively larger or smaller gap. As shown, the larger angle $\beta$ results in a relatively more narrow distal tip when the snare device 110 is in a collapsed and/or compressed state. This reduced profile can result in easier and safer insertion and removal of snare device 110 from a patient's body. In either arrangement, however, second stabilizer 106 and 116 may facilitate increased stability in snare devices 100 and 110, respectively, by preventing snare devices 100 and 110 from bending and/or deflecting away from a plane of a layer of tissue, which may reduce the snare's ability to ensnare the desired tissue during resecting, grasping, and/or collecting tissue via snare devices 100 and 110. That is, stabilizers 106 and 116 may resist forces (including torsional forces) imparted to snare devices 100 and 110 during use.

In a further example, as shown in FIG. 11, an exemplary snare device 120 may include an atraumatic tip 122. The example of FIG. 11 may include one or more features described above in connection with FIGS. 1A and 1B. In addition, the legs of the snare device 120 may include a thickness different than a thickness at a distal portion of atraumatic tip 122. For example, a distal portion of atraumatic tip 122 may have a first thickness A while legs 125 of snare device 120 may have a second thickness B. As shown in FIG. 11, first thickness A may be greater than second thickness B. That is, a ratio of A to B may be greater than 1. The increased thickness or material of the distal portion of atraumatic tip 122 may prevent snare device 120 from bending and/or deflecting away from a plane of a layer of tissue, which may reduce the snare's ability to ensnare the desired tissue during resecting, grasping, and/or collecting tissue via snare device 120. That is, the increased thickness A may resist forces (including torsional forces) imparted to snare device 120 during use. Additionally, the example of FIG. 11 may include one or more features described above in connection with FIGS. 2, 3, 4A, 4B, 5-8, 9A, 9B, 10A, and 10B, such as, for example, one or more additional stabilizers.

Figure 12:
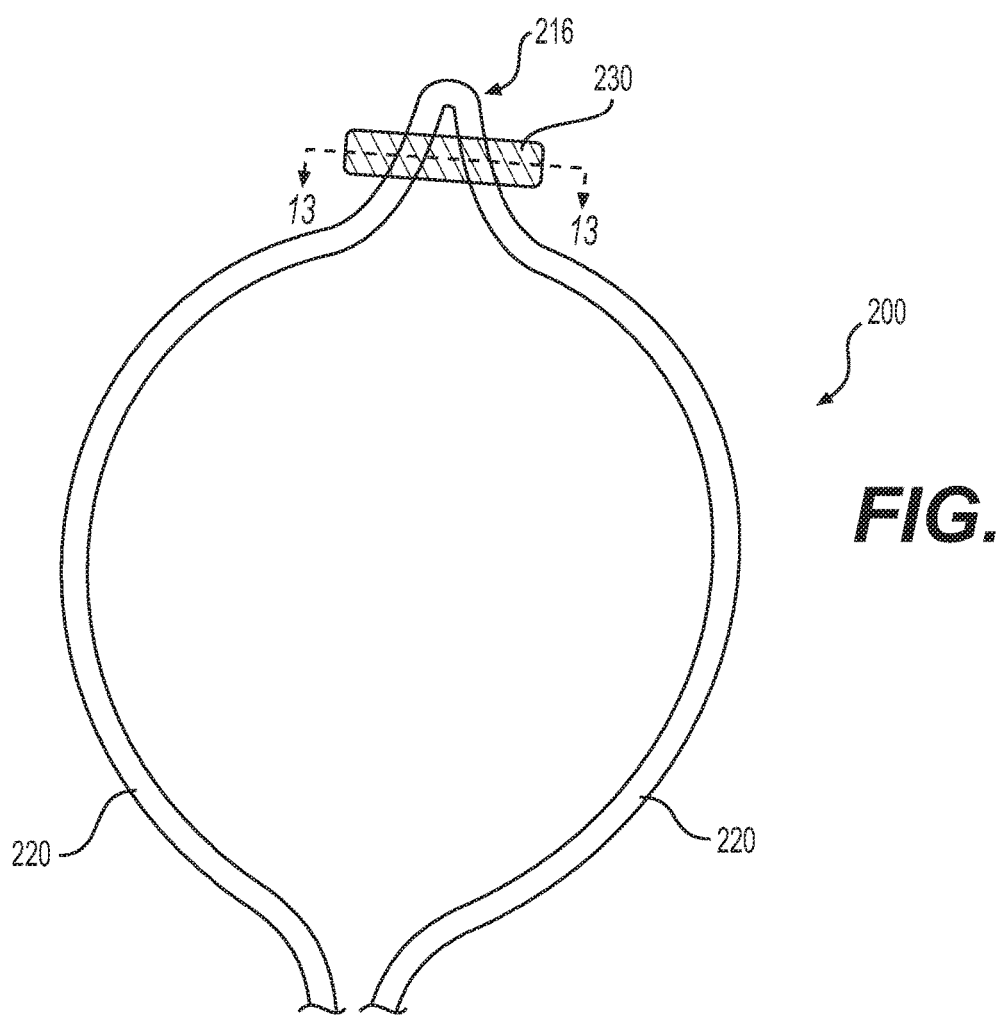
FIG. 12 depicts a side view of an exemplary snare device in an extended state and having a securement member.

FIG. 12 depicts a side-view of an additional exemplary snare device 200. The example of FIG. 12 may include one or more features described above in connection with FIGS. 1A and 1B. For example, snare device 200 may be a single, continuous monofilament or multifilament piece of material such as wire including legs 220 formed in a loop. The snare loop may further include teeth or the like (not shown) configured for cutting and/or grasping tissue therewith. Legs 220 may extend proximally and may be associated with any appropriate user interface such as, for example, a handle (not shown). Alternatively, legs 220 may terminate proximally of a handle. As such, a proximal end of legs 220 may be coupled to an actuating member (not shown) via a securement device such as, for example, a hypotube or crimp (not shown). The handle may be configured to remain outside of the patient's body during a procedure and may allow a user to control the snare device 200, for example, by applying an axially directed pushing or pulling force on one or both of the legs 220.

Figure 13:
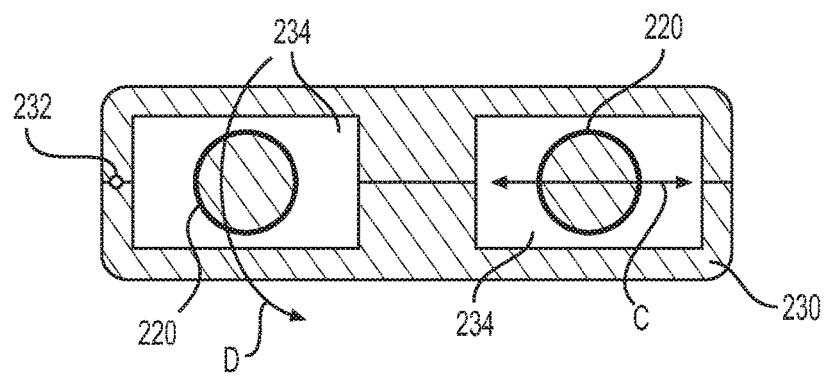
FIG. 13 is a cross-sectional view of the exemplary securement member of FIG. 12 taken along line 13-13 of FIG. 12.

Snare device 200 may include any appropriate material, such as, for example, Nitinol. Snare device 200 may be heat set into an arcuate, circular, or otherwise curved shape as shown in FIG. 12, and may include an atraumatic tip 216. As shown in FIG. 12, a clip, fastener, snap, buckle, clasp, and/or securement member 230 is coupled to atraumatic tip 216. Securement member 230 may have an appropriate shape. For example, securement member 230 may have a generally rectangular shape having rounded corners. It is noted, however, that the disclosure is not so limited. Rather, any appropriate shape may be used. Securement member 230 may be a one-piece monolithically-formed construction (FIG. 12). Accordingly, legs 220 may be routed through securement member 230 prior to associating legs 220 with an appropriate actuator. Alternatively, however, securement member 230 may include a two-piece clam shell construction and may optionally include a hinge or pivot point 232 (FIG. 13) enabling two halves of securement member 230 to open and close so as to irremovably receive legs 220 of snare device 200 therein. In either arrangement, securement member 230 may define a pair of through passageways or channels 234, as shown in FIG. 13.

Each channel 234 may receive a portion of a leg 220 of the snare device 200 therein. As shown, each channel 234 may be sized such that a leg 220 may slide freely therethrough. That is, each channel 234 may receive a leg 220 with sufficient clearance so as not to impede or interfere with movement of the leg 220 in channel 234 along a longitudinal axis of the channel 234. However, channels 234 of securement member 230 may limit translation movement of legs 220 along line C and rotational movement or torsion of legs 220 along arrow D. That is, securement member may inhibit translation of legs towards or away from one another, and/or rotation about one another. In such a manner, securement member 230 may reduce the degree of freedom of each leg 220 of the snare device 200, and thus, prevent snare device 220 from bending and/or deflecting away from a plane of a layer of tissue, which may reduce the snare's ability to ensnare the desired tissue during resecting, grasping, and/or collecting tissue via snare device 200.

FIGS. 14A-14E depict an additional exemplary snare device 300. The example of FIGS. 14A-14E may include one or more features described above in connection with FIGS. 1A and 1B. Snare device 300 may be a single, continuous monofilament or multifilament piece of material such as wire including legs 320 and may be manipulated so as to form a loop. That is, the continuous wire of snare device 300 may be overlapped upon itself so as to form a distal atraumatic tip or loop 350. For example, the wire of snare device 300 may be pre-formed, machined, or otherwise fabricated to include various cross-sectional shapes and features (e.g., a pin hole for receiving a pin 360 to connect two overlapping portions of device 300), and subsequently folded, bent, pleated, or otherwise caused to over lay itself thereby forming loop 350. In order to maintain loop 350, a pin 360 may be extended through holes preformed in the wire of snare device 300, to retain its shape. By virtue of pin 360 being extended through the wire of snare device 300, pin 360 may be configured to prevent snare device 300 from bending and/or deflecting away from a plane of a layer of tissue, which may reduce the snare's ability to ensnare the desired tissue during resecting, grasping, and/or collecting tissue via snare device 300.

Legs 320 may extend proximally and may be associated with any appropriate user interface such as, for example, a handle (not shown). Alternatively, legs 320 may terminate proximally of a handle. As such, a proximal end of legs 320 may be coupled to an actuating member (not shown) via a securement device such as, for example, a hypotube or crimp (not shown). The handle may be configured to remain outside of the patient's body during a procedure and may allow a user to control the snare device 300, for example, by applying an axially directed pushing or pulling force on one or both of the legs 320.

Figure 14:
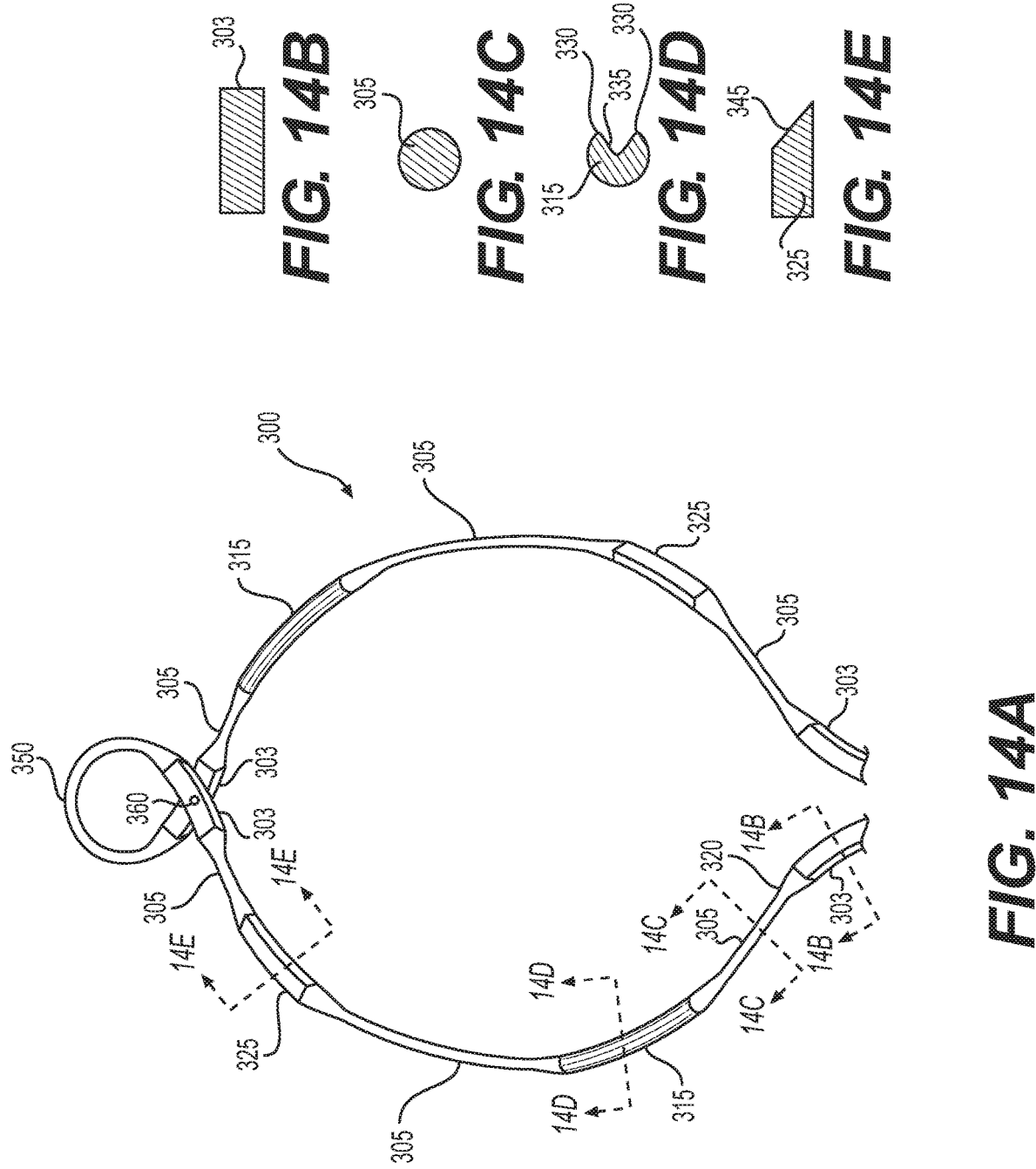
FIG. 14A depicts a side view of an exemplary snare device in an extended state and having a varied cross-sectional profile.
FIG. 14B is a cross-sectional view of the exemplary snare device of FIG. 14A taken along line 14B-14B of FIG. 14A.
FIG. 14C is a cross-sectional view of the exemplary snare device of FIG. 14A taken along line 14C-14C of FIG. 14A.
FIG. 14D is a cross-sectional view of the exemplary snare device of FIG. 14A taken along line 14D-14D of FIG. 14A.
FIG. 14E is a cross-sectional view of the exemplary snare device of FIG. 14A taken along line 14E-14E of FIG. 14A.

Snare device 300 may include any appropriate material, such as, for example, Nitinol. Snare device 300 may have a varied cross-section along its length. For example, snare device 300 may include first portions 303, second portions 305, third portions 315, and fourth portions 325 disposed along its length. For example, as shown in FIG. 14B, first portions 303 may have a rectangular cross-sectional shape. Upon formation, first portions 303 adjacent a proximal end of snare device 300 may facilitate in-plane stability of snare device 300. That is, the rectangular cross-sectional shape of first portions 303 adjacent a proximal end of snare device 300 may prevent snare device from distorting away from the plane of tissue to be resected and/or treated. Additionally, first portions 303 adjacent loop 350 may facilitate alignment of pin holes therethrough for receiving pin 360. That is, the flattened cross-sectional shape of first portions 303 may enable quick machining to enable insertion of pin 360 therethrough.

Second portions 305, as shown in FIG. 14C, may have a circular cross-sectional shape, while third portions 315, as shown in FIG. 14D, may include a circular cross-section with a wedge shaped cut out 335 defining pointed and/or sharp edges or ridges 330. In use, cut out 335 may receive and retain tissue therein. That is, upon tissue being lifted, as will be described in further detail below, and/or engaging with third portions 315, cut out 335 may be configured to grasp, grip, hold, and/or maintain tissue therein. Accordingly, cut out 335 may be configured to maintain contact with tissue during resection and/or removal. Additionally, ridges 330 may facilitate grasping, lifting, and/or cutting tissue. Further, fourth portions 325 may include a planar configuration having a tapered, angled, or otherwise wedge-shaped edge 345. In use, edge 345 may be configured to lift tissue from a surface of a body passage or cavity. That is, edge 345 may urge, force, or otherwise drive tissue along edge 345 so as to lift tissue. Additionally, edge 345 may be sharp, such that edge 345 may penetrate, pierce, or otherwise cut tissue. Accordingly, cut out 335 and edge 345 may collectively lift, retain, and cut tissue. Additionally, as shown in FIG. 14A, each transition between first portions 303, second portions 305, third portions 315, and/or fourth portions 325 may be gradual, angled, or otherwise tapered as shown. However, in some examples, each such transitions may be sharp and/or non-tapered.

Figure 15:
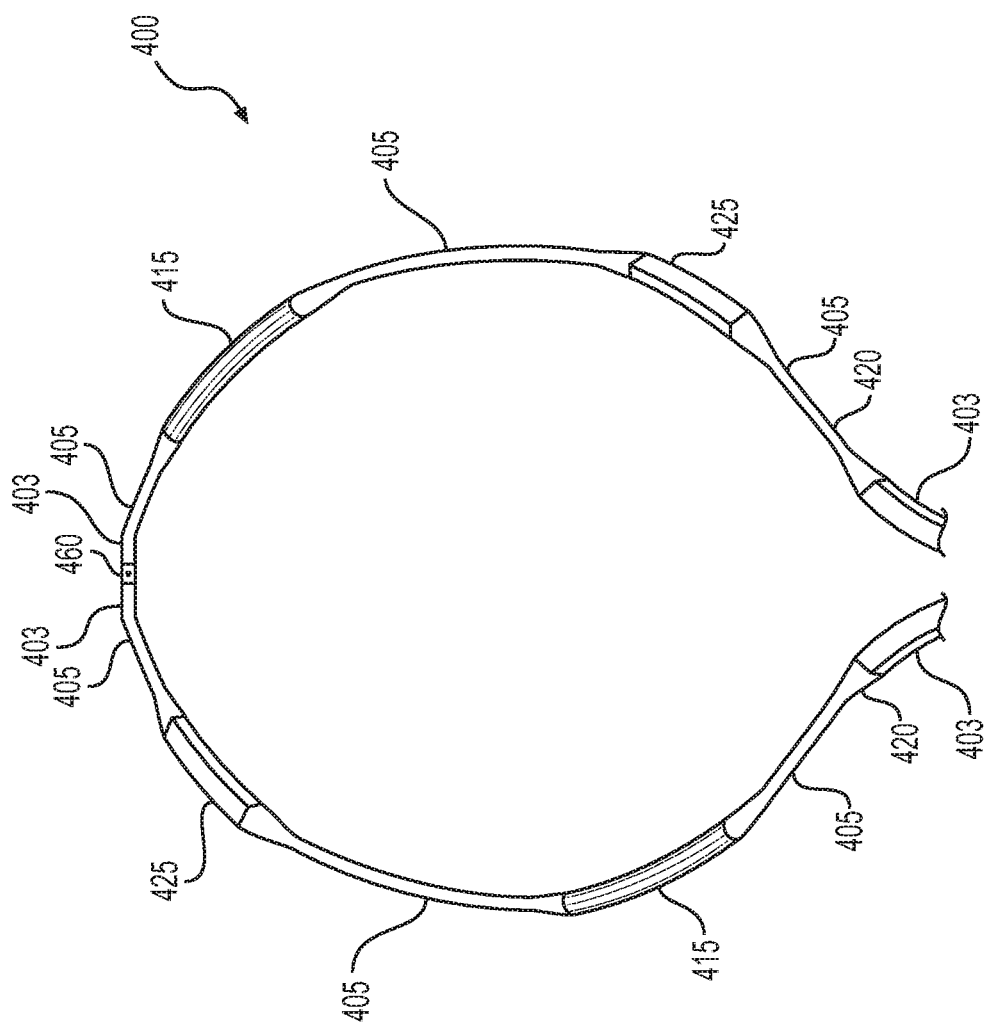
FIG. 15 depicts a side view of another exemplary snare device in an extended state and having a varied cross-sectional profile.

FIG. 15 depicts an additional exemplary snare device 400. The example of FIG. 15 may be similar in construction to, and/or include one or more features described above in connection with FIGS. 14A-14E, and accordingly, like components have been given like reference numerals plus 100 and only the differences between snare device 400 and snare device 300 will be discussed in detail below. Snare device 400 may include a wire including legs 420. Rather than being a continuous wire overlapped upon itself so as to form a distal atraumatic tip or loop, such as loop 350 of FIG. 14A, snare device 400 may be comprised of two separate and distinct legs 420 coupled to one another so as to form a loop. In order to couple legs 420, a pin 460 may be extended through overlapping portions of legs 420 at the tip of snare device 400 to retain its shape. By virtue of overlapped portions of legs 420 and pin 460, snare device 400 may be prevented from bending and/or deflecting away from a plane of a layer of tissue, which may reduce the snare's ability to ensnare the desired tissue during resecting, grasping, and/or collecting tissue via snare device 400.

While principles of the present disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A medical device, comprising:
    a snare loop including a first leg, a second leg, and a tip joining a distal end of the first leg to a distal end of the second leg, wherein the tip includes a first stabilizer and a second stabilizer, wherein a portion of the first stabilizer is distal to the second stabilizer, wherein the first stabilizer extends from the distal end of the first leg to the distal end of the second leg, wherein the second stabilizer extends from the distal end of the first leg to the distal end of the second leg, wherein the distal end of the first leg is proximal of the distal end of the second leg, wherein an obtuse angle is formed between the second stabilizer and the distal end of the first leg, wherein an acute angle is formed between the second stabilizer and the distal end of the second leg, and wherein the first leg, the second leg, all of the first stabilizer, and all of the second stabilizer lie in a single, common plane.

2. The medical device of claim 1, further comprising:
an insertion device having a proximal end, a distal end, and a lumen extending therethrough;
wherein the snare loop is configured to transition between a contracted state in which the snare loop is within the lumen of the insertion device, and an expanded state in which the snare loop extends distally of the insertion device.

3. The medical device of claim 2, wherein a gap is between a portion of the first stabilizer and a portion of the second stabilizer in both the contracted state and the expanded state.

4. The medical device of claim 1, wherein the tip includes only two stabilizers.

5. The medical device of claim 1, wherein the first leg, the second leg, the first stabilizer, and the second stabilizer are monolithically formed of a common material.

6. The medical device of claim 1, wherein the first stabilizer, the first leg, and the second leg form a contiguous loop, and wherein the second stabilizer is affixed to the contiguous loop via soldering, welding, or adhesive.

7. The medical device of claim 1, wherein the first stabilizer extends from the first leg at a first angle, and wherein the first stabilizer extends from the second leg at a second angle, different from the first angle.

8. A medical device, comprising:
a snare loop including:
  a first leg;
  a second leg;
  a first stabilizer having a first portion extending distally from a distal end of the first leg and a second portion extending distally from a distal end of the second leg, wherein the first portion and the second portion are joined at a first distal tip, wherein the first distal tip is pointed in a first direction; and
  a second stabilizer having a first portion extending distally from the distal end of the first leg and a second portion extending distally from the distal end of the second leg, wherein the first portion of the second stabilizer and the second portion of the second stabilizer are joined at a second distal tip, wherein the second distal tip is pointed in a second direction, opposite the first direction, wherein the distal end of the first leg is proximal of the distal end of the second leg.

9. The medical device of claim 8, further comprising:
an insertion device having a proximal end, a distal end, and a lumen extending therethrough;
wherein the snare loop is configured to transition between a contracted state in which the snare loop is within the lumen of the insertion device, and an expanded state in which the snare loop extends distally of the insertion device.

10. The medical device of claim 9, wherein a gap is between a portion of the first stabilizer and a portion of the second stabilizer in both the contracted state and the expanded state.

11. The medical device of claim 8, wherein the snare loop consists essentially of the first leg, the second leg, the first stabilizer, and the second stabilizer.

12. The medical device of claim 8, wherein the second stabilizer extends from the first leg at a first angle, and wherein the second stabilizer extends from the first leg at a second angle, different from the first angle.

13. A medical device, comprising:
a snare loop including a first leg, a second leg, and a tip joining a distal end of the first leg to a distal end of the second leg, wherein the tip includes a first stabilizer and a second stabilizer, wherein the first stabilizer includes a first distal tip pointed in a first direction, wherein the second stabilizer includes a second distal tip pointed in a second direction opposite the first direction, and wherein the first leg, the second leg, all of the first stabilizer, and all of the second stabilizer lie in a single, common plane.

14. The medical device of claim 13, further comprising:
an insertion device having a proximal end, a distal end, and a lumen extending therethrough;
wherein the snare loop is configured to transition between a contracted state in which the snare loop is within the lumen of the insertion device, and an expanded state in which the snare loop extends distally of the insertion device.

15. The medical device of claim 13, wherein the first stabilizer is asymmetrical relative to the longitudinal axis, and wherein the second stabilizer is symmetrical relative to the longitudinal axis.

16. The medical device of claim 13, wherein a distal tip of the first stabilizer is distal to a distal tip of the second stabilizer.

17. The medical device of claim 13, wherein the tip includes only two stabilizers.

* * * * *